(12) United States Patent
Baran, Jr. et al.

(10) Patent No.: US 8,951,541 B2
(45) Date of Patent: Feb. 10, 2015

(54) METHOD OF MODIFYING DISSOLUTION RATE OF PARTICLES BY ADDITION OF HYDROPHOBIC NANOPARTICLES

(75) Inventors: Jimmie R. Baran, Jr., Prescott, WI (US); Haeen Sykora, New Richmond, WI (US); Rebecca L. A. Everman, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 48 days.

(21) Appl. No.: 13/811,854

(22) PCT Filed: Sep. 28, 2011

(86) PCT No.: PCT/US2011/053596
§ 371 (c)(1),
(2), (4) Date: Jan. 23, 2013

(87) PCT Pub. No.: WO2012/047691
PCT Pub. Date: Apr. 12, 2012

(65) Prior Publication Data
US 2013/0195938 A1    Aug. 1, 2013

Related U.S. Application Data

(60) Provisional application No. 61/389,401, filed on Oct. 4, 2010.

(51) Int. Cl.
*A61K 9/14* (2006.01)
*B82Y 30/00* (2011.01)

(52) U.S. Cl.
CPC .. *A61K 9/14* (2013.01); *B82Y 30/00* (2013.01)
USPC .......................................... 424/400; 514/629

(58) Field of Classification Search
None
See application file for complete search history.

(56) References Cited

U.S. PATENT DOCUMENTS

| | | | |
|---|---|---|---|
| 5,019,302 A * | 5/1991 | Sparks et al. | 264/8 |
| 2002/0045045 A1 | 4/2002 | Adams | |
| 2003/0102099 A1 | 6/2003 | Yadav | |
| 2003/0203019 A1 * | 10/2003 | Cornelius et al. | 424/465 |
| 2004/0242729 A1 * | 12/2004 | Baran et al. | 523/200 |
| 2006/0008618 A1 * | 1/2006 | Wang et al. | 428/143 |
| 2008/0070030 A1 * | 3/2008 | Baran et al. | 428/323 |
| 2008/0152913 A1 | 6/2008 | Shinbach | |
| 2008/0153963 A1 | 6/2008 | Baran | |
| 2008/0286362 A1 | 11/2008 | Baran, Jr. | |
| 2010/0116172 A1 * | 5/2010 | Baran et al. | 106/277 |
| 2011/0076336 A1 * | 3/2011 | Cantor et al. | 424/490 |
| 2012/0233929 A1 * | 9/2012 | Baran et al. | 51/308 |

FOREIGN PATENT DOCUMENTS

| | | |
|---|---|---|
| WO | WO 2007/019229 | 2/2007 |
| WO | WO 2008/079650 | 7/2008 |
| WO | WO 2009/085926 | 7/2009 |
| WO | WO 2010/151435 | 12/2010 |

OTHER PUBLICATIONS

Saharan, "Dissolution enhancement of drugs. Part I: Technologies and effect of carriers" *International Journal of Health Research*, vol. 2, No. 2, pp. 107-124 (Jun. 2, 2009).
http://www.fpharm.uniba.sk/fileadmin/user_upload/english/Physical_Chemistry/4-Dissolution_of_solid_substances.pdf retrieved from web Oct. 22, 2010.

* cited by examiner

*Primary Examiner* — Robert A Wax
*Assistant Examiner* — Danah Al-Awadi
(74) *Attorney, Agent, or Firm* — Kent S. Kokko

(57) ABSTRACT

Method of modifying dissolution rate of a plurality of particles in an aqueous-based solvent by adding hydrophobic surface modified nanoparticles to the plurality of particles, and exposing the plurality of particles to the aqueous-based solvent.

20 Claims, 11 Drawing Sheets

METHOD OF MODIFYING DISSOLUTION RATE OF PARTICLES BY ADDITION OF HYDROPHOBIC NANOPARTICLES

BACKGROUND

WO 2008/079650, published Jul. 3, 2008, and WO 2007/019229, published Feb. 15, 2007, report adding nanoparticles to particles for the purpose of improving the flow properties.

SUMMARY

In one aspect, the present disclosure provides a method of modifying dissolution rate of a plurality of particles, the method comprising:
providing a plurality of particles having a solubility in an aqueous-based solvent;
adding hydrophobic surface modified nanoparticles; and
exposing the plurality of particles to the aqueous-based solvent; wherein the plurality of particles combined with the hydrophobic surface modified nanoparticles have a modified (i.e., an increased or decreased) dissolution rate in the aqueous-based solvent relative to a dissolution rate of the plurality of particles in the aqueous-based solvent without the presence of hydrophobic surface modified nanoparticles.

In some embodiments, the aqueous-based solvent is water. In some other embodiments, the aqueous-based solvent comprises a mixture of water and a water-miscible polar organic solvent.

In some embodiments, the method of the current description is useful for modifying the rate of dissolution of particles during, for example, the formulation of materials for the production of roofing granules.

DETAILED DESCRIPTION

Figure 1:
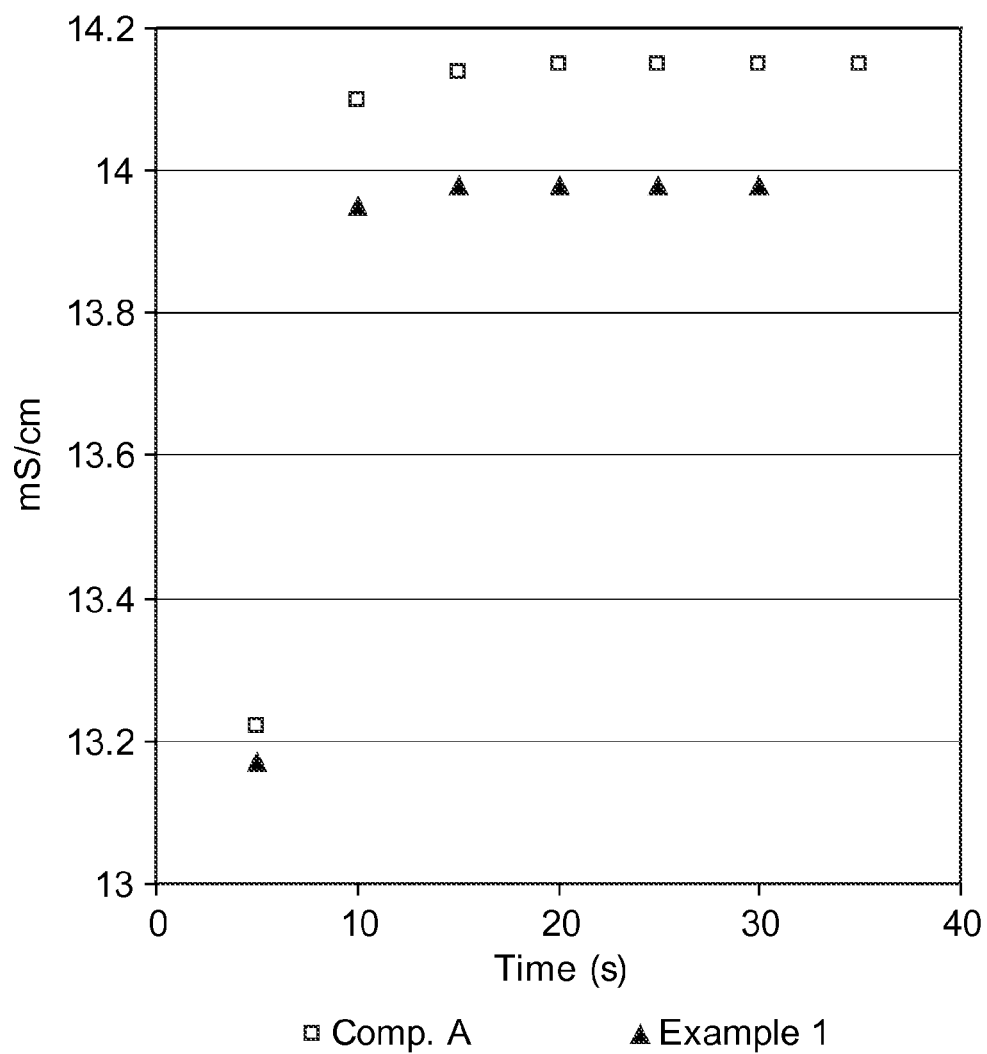
FIG. 1 is a plot of conductance versus time data for Example 1 and Comparative Example A.

In general, the dissolution rate of a plurality of particles having a solubility in an aqueous-based solvent can be modified by adding hydrophobic surface modified nanoparticles to the plurality of particles, and exposing the plurality of particles to the aqueous-based solvent.

The term "aqueous-based solvent" refers to a solvent for the particles that includes water. An aqueous-based solvent can be entirely water, or can also contain a polar organic solvent that is miscible with water. In some embodiments, the polar organic solvent may be added to increase the solubility of particles in the aqueous-based solvent. Suitable polar organic solvents include alcohols, dimethylsulfoxide, dimethylformamide, N-methylpyrrolidone, acetonitrile, acetone, and tetrahydrofuran. In some embodiments, the polar organic solvent is an alcohol having up to 6 carbon atoms, up to 5 carbon atoms, up to 4 carbon atoms, up to 3 carbon atoms, or even up to 2 carbon atoms. In some embodiments, the volume ratio of water to polar organic solvent is in the range of 1:10 to 1:0.1. For example, the volume ratio of water to polar organic solvent can be in the range of 1:5 to 1:0.5 or 1:2 to 1:0.2. In some embodiments, the volume % of water in the aqueous-based solvent can be at least 75%, 70%, 65%, 60%, 55%, 50%, 45%, 40%, 35%, 30%, 25%, 20%, 15%, 10%, 5%, 1%, or even at least 0.1%. The particles of the current description have a solubility in the aqueous-based solvent, and the minimum amount of water to be included in the aqueous-based solvent depends upon the solubility of the particle materials in the aqueous-based solvent. The solubility is commonly expressed in the art as a solubility product ("$K_{SP}$") value. In embodiments where water and polar organic solvent are being combined, the amount of water does not exceed the miscibility of water in the polar organic solvent.

The particles may be distinguished from the nanoparticles by relative size. The particles are larger than the nanoparticles.

The particles have a median primary or agglomerate particle size (generally measured as an effective diameter) of at least 100 nm (i.e. 0.1 micrometers), 200 nm, 300 nm, 400 nm, or 500 nm. The median particle size is typically up to about 1,000 micrometers and more typically up to 500 micrometers, 400 micrometers, 300 micrometers, or even up to 200 micrometers. In some embodiments, the particles have a polymodal (e.g., bi-modal or tri-modal) distribution.

The term "agglomerate" refers to a weak association between primary particles or primary nanoparticles which may be held together by charge or polarity and can be broken down into smaller entities. The terms "primary particle size" and "primary nanoparticle size" refer to the mean diameter of a single (non-aggregate, non-agglomerate) particle or nanoparticle, respectively.

The hydrophobic surface modified nanoparticles have an average primary or agglomerate nanoparticle size diameter of up to 100 nanometers. In some embodiments, the nanoparticles have an average nanoparticle size of up to 75 nanometers or even up to 50 nanometers. The nanoparticles typically have an average primary or agglomerate nanoparticle size diameter of at least 3 nanometers. In some preferred embodiments, the average primary or agglomerate nanoparticle size is up to 20 nm, 15 nm, or even up to 10 nm. Nanoparticle measurements can be based on, for example, transmission electron microscopy (TEM).

The particles typically have a median primary particle size of at least 50, 60, 70, 80, 90, or even at least 100 times larger than the mean nanoparticle size of the hydrophobic surface modified nanoparticles. In some embodiments, the larger particles have a median primary particle size of at least 200, 300, 400, 500, 600, 700, or even at least 800 times larger than the mean nanoparticle size of the hydrophobic surface modified nanoparticles. The larger particles may have a median primary particle size up to 5,000 or even up to 10,000 times larger than the mean nanoparticle size of the hydrophobic surface modified nanoparticles.

In general, particles of the current description can include inorganic particles, organic particles, and combinations thereof.

In some embodiments, inorganic particle materials include metal phosphates, sulfonates and carbonates (e.g., calcium carbonate, calcium phosphate, hydroxy-apatite) that have solubility in the aqueous-based solvent. In some embodiments, the inorganic particle material can include any of borax, calcium chloride, calcium hydroxide, magnesium chloride, magnesium sulfate, sodium chloride, sodium sulfite, and anhydrous or hydrated particle forms thereof.

In some embodiments, the particles may comprise organic materials having a solubility in an aqueous-based solvent, including polymers, cosmetic agents, pharmaceutical agents, and excipients (i.e. an inactive substance used as a carrier for the active ingredient of a medication). In some embodiments, the organic particle material comprises lactose.

Pharmaceutical agents can include antiallergics, analgesics, bronchodilators, antihistamines, therapeutic proteins and peptides, antitussives, anginal preparations, antibiotics, anti-inflammatory preparations, diuretics, hormones, or sulfonamides (e.g., a vasoconstrictive amine, an enzyme, an alkaloid or a steroid), and combinations of any one or more of these. A specific example of a pharmaceutical agent is acetaminophen.

While inorganic nanoparticles lacking a surface treatment are generally hydrophilic, methods of modifying the surface with a hydrophobic surface treatment are well known. Surface modification involves attaching surface modification agents to inorganic oxide particles to modify the surface characteristics. In general, a surface treatment has a first end that will attach to the nanoparticle surface (covalently, ionically or through strong physisorption) and a second end that imparts steric stabilization that prevents the particles from agglomerating such as permanently fusing together. The inclusion of surface modification can also improve the compatibility of the particles with other materials. For example, an organic end group such as the organic group of an organosilane can improve the compatibility of the particles with organic matrix material such as polymerizable and thermoplastic resins.

In some embodiments, the hydrophobic surface modified nanoparticles of the present description comprise inorganic nanoparticles that have a hydrophobic surface treatment. In some embodiments the inorganic nanoparticles comprise an inorganic material such as a metal oxide. Various inorganic nanoparticles are commercially available. In some embodiments, the nanoparticles comprise silica, zirconia, or a mixture thereof. Commercial sources of silica nanoparticles are available, for example, from Nalco Co, Napervillle, Ill. Inorganic nanoparticles can also be made using techniques known in the art. Zirconia nanoparticle can also be prepared, for example, using hydrothermal technology, as described in WO 2009/085926 (Kolb et al.), published Jul. 9, 2009, the description of which is incorporated herein by reference.

In some embodiments, the (non-surface modified) nanoparticles may be in the form of a colloidal dispersion. Colloidal silica dispersions are available, for example, from Nalco Co. under the trade designations "NALCO 1040," "NALCO 1050," "NALCO 1060," "NALCO 2327," and "NALCO 2329". Zirconia nanoparticle dispersions are available, for example, from Nalco Chemical Co. under the trade designation "NALCO OOSSOO8" and from Buhler AG Uzwil, Switzerland under the trade designation "BUHLER ZIRCONIA Z-WO". Some colloidal dispersions, especially of surface modified nanoparticles, can be dried to provide nanoparticles for dry milling processes.

Examples of surface treatment agents include alcohols, amines, carboxylic acids, sulfonic acids, phosphonic acids, silanes and titanates. The preferred type of treatment agent is determined, in part, by the chemical nature of the (e.g. metal oxide) nanoparticle surface. Silanes are preferred for silica and for other siliceous fillers. Silanes and carboxylic acids are preferred for metal oxides such as zirconia. When an organosilane surface treatment is applied to metal oxide nanoparticles, the silane end is generally adsorbed by the nanoparticle. When a carboxylic acid is applied to a zirconia nanoparticle, the acid end is generally adsorbed by the zirconia.

Exemplary silanes include alkyltrialkoxysilanes (e.g., n-octyltrimethoxysilane, n-octyltriethoxysilane, isooctyltrimethoxysilane, dodecyltrimethoxysilane, octadecyltrimethoxysilane, propyltrimethoxysilane, and hexyltrimethoxysilane); methacryloxyalkyltrialkoxysilanes or acryloxyalkyltrialkoxysilanes (e.g., 3-methacryloxypropyltrimethoxysilane, 3-acryloxypropyltrimethoxysilane, and 3-(methacryloxy)propyltriethoxysilane); methacryloxyalkylalkyldialkoxysilanes and acryloxyalkylalkyldialkoxysilanes (e.g., 3-(methacryloxy)propylmethyldimethoxysilane and 3-(acryloxypropyl)methyldimethoxysilane); methacryloxyalkyldialkylalkoxysilanes and acryloxyalkyldialkylalkoxysilanes (e.g., 3-(methacryloxy)propyldimethylethoxysilane); mercaptoalkyltrialkoxylsilanes (e.g., 3-mercaptopropyltrimethoxysilane); aryltrialkoxysilanes (e.g., styrylethyltrimethoxysilane, phenyltrimethoxysilane, phenyltriethoxysilane, and p-tolyltriethoxysilane); vinyl silanes (e.g., vinylmethyldiacetoxysilane, vinyldimethylethoxysilane, vinylmethyldiethoxysilane, vinyltrimethoxysilane, vinyltriethoxysilane, vinyltriacetoxysilane, vinyltriisopropoxysilane, vinyltrimethoxysilane, vinyltriphenoxysilane, vinyltri-t-butoxysilane, vinyltris(isobutoxy)silane, vinyltriisopropenoxysilane, and vinyltris(2-methoxyethoxy)silane); and combinations thereof.

Carboxylic acid surface modifying agents may comprise, for example, the reaction product of phthalic anhydride with an organic compound having a hydroxyl group. Suitable examples include phthalic acid mono-(2-phenylsulfanyl-ethyl) ester, phthalic acid mono-(2-phenoxy-ethyl) ester, or phthalic acid mono-[2-(2-methoxy-ethoxy)-ethyl] ester. In some examples, the organic compound having a hydroxyl group is a hydroxyl alkyl(meth)acrylate such as hydroxyethyl (meth)acrylate, hydroxypropyl(meth)acrylate, or hydroxylbutyl(meth)acrylate. Examples include succinic acid mono-(2-acryloyloxy-ethyl) ester, maleic acid mono-(2-acryloyloxy-ethyl) ester, glutaric acid mono-(2-acryloyloxy-ethyl) ester, phthalic acid mono-(2-acryloyloxy-ethyl) ester, and phthalic acid mono-(2-acryloyl-butyl) ester. Still others include mono-(meth)acryloxy polyethylene glycol succinate and the analogous materials made from maleic anhydride glutaric anhydride, and phthalic anhydride. In another example, the surface modification agent is the reaction product of polycaprolactone and succinic anhydride such as described in WO 2010/074862 (Jones et al.), published Jul. 1, 2010, the description of which is incorporated herein by reference. Various other surface treatments are known in the art, such as described in WO 2007/019229 (Baran et al.), published Feb. 15, 2007, the description of which is incorporated herein by reference.

The surface treatment may comprise a blend of two or more hydrophobic surface treatments. For example, the surface treatment may comprise at least one surface treatment having a relatively long substituted or unsubstituted hydrocarbon group. In some embodiments, the surface treatment comprises at least one hydrocarbon group having at least 6 or 8 carbon atoms, (e.g., isooctyltrimethoxysilane), with a second surface treatment that is less hydrophobic (e.g., methyltrimethoxysilane).

The surface treatment may also comprise a blend of a hydrophobic surface treatment and (e.g., a small concentration of) a hydrophilic surface treatment, provided that the inclusion of such does not detract from the modification of dissolution rate as contributed by the hydrophobic surface treatment(s).

In general, the nanoparticles are combined with the surface modification prior to mixing the nanoparticle with the particles. The amount of surface modifier is dependant upon several factors such as nanoparticle size, nanoparticle type, molecular weight of the surface modifier, and modifier type. In general, it is preferred that approximately a monolayer of modifier is attached to the surface of the nanoparticle. The attachment procedure or reaction conditions also depend on the surface modifier used. For silanes it is preferred to surface treat at elevated temperatures under acidic or basic conditions for about 1-24 hour. Surface treatment agents such as carboxylic acids do not require elevated temperatures or extended time.

The surface modification of the nanoparticles in the colloidal dispersion can be accomplished in a variety of ways. The process involves the mixture of an inorganic dispersion with surface modifying agents. Optionally, a co-solvent can be added at this point, such as for example, 1-methoxy-2-propanol, methanol, ethanol, isopropanol, ethylene glycol, N,N-dimethylacetamide, 1-methyl-2-pyrrolidinone, and mixtures thereof. The co-solvent can enhance the solubility of the surface modifying agents as well as the dispersibility of the surface modified nanoparticles. The mixture comprising the inorganic sol and surface modifying agents is subsequently reacted at room or an elevated temperature, with or without mixing.

In some embodiments, the hydrophobic surface modified nanoparticles are added to the plurality of particles as discrete hydrophobic surface modified nanoparticles. In some embodiments, the hydrophobic surface modified nanoparticles are added as discrete hydrophobic surface modified nanoparticles. In some embodiments, the hydrophobic surface modified nanoparticles have a primary nanoparticle size of up to 100 nanometers.

In many embodiments, the hydrophobic (e.g., surface modified) nanoparticles will be present in an amount up to 10 weight percent solids of the total mixture of particles and nanoparticles. In some embodiments, the hydrophobic nanoparticles are present in an amount up to about 5, 4, 3, or even up to about 2 weight percent solids. The amount of hydrophobic nanoparticles is typically at least 0.01 wt %, 0.05 wt %, or even at least 0.1 wt % solids. In some embodiments, the amount of hydrophobic nanoparticles is at least 0.2 wt % solids, 0.3 wt % solids, 0.4 wt % solids, or even at least 0.5 wt % solids. However, if the particles are a concentrated master batch, the concentration of hydrophobic nanoparticles may be substantially higher.

In some embodiments, the method comprises providing a plurality of particles having a solubility in an aqueous-based solvent, and adding hydrophobic surface modified nanoparticles, without the addition of a volatile inert liquid that is not a solvent with respect to the particles. In some other embodiments, the method comprises providing a mixture comprising a plurality of particles having a solubility in an aqueous-based solvent, and adding hydrophobic surface modified nanoparticles as a colloidal dispersion in a volatile inert liquid that is not a solvent with respect to the particles. Typical liquids that may be employed for the colloidal dispersion include toluene, isopropanol, heptane, hexane, and octane. The concentration of liquid in the mixture is up to 5 wt %. In some embodiments, the concentration of liquid in the mixture is up to 4 wt %, up to 3 wt %, up to 2 wt %, up to 1 wt %, or even up to 0.5 wt %. The concentration of liquid in the mixture is sufficiently small such that the liquid evaporates during mixing. If a higher concentration of liquid is employed, the method then typically further comprises removing the liquid from the mixture, for example, by filtering and/or evaporation to recover a free-flowing dry powder of the plurality of particles combined with the hydrophobic surface modified nanoparticles.

The mixture of particles and hydrophobic surface modified nanoparticles can optionally be milled such that the milled particles have a reduced particle size as described in International Patent Application No. PCT/US2010/038,132 (Shinbach et al.), filed Jun. 10, 2010, the description of which is incorporated herein by reference.

The time period required to a leveling off in the dissolution of the plurality of particles of the current description can vary from about 1 or 2 seconds, up to minutes, up to several hours, or even up to several days. Without limiting the scope of the current description, the time period required to a leveling off in the dissolution of the plurality of particles of the current description can depend on variables that include the selection of aqueous-based solvent, particle size and shape, temperature, mixing, sonication, and the inclusion of acids, bases, and/or electrolytes. Those having skill in the art can select a reasonable time period required for dissolution of the plurality of particles, for example, in Example 1 (discussed below) a leveling off of dissolution occurs within 1 minute. The inclusion of the hydrophobic surface modified nanoparticles with particle materials of the current description can provide various beneficial properties to the resulting composition, and in particular a modification of the dissolution rate of the particulate material in the aqueous-based solvent.

In some embodiments, the modified dissolution rate in the aqueous-based solvent is higher than the dissolution rate of the plurality of particles in the aqueous-based solvent without the presence of hydrophobic surface modified nanoparticles. In some embodiments, the modified dissolution rate in the aqueous-based solvent is at least 1% higher, at least 5% higher, or even at least 10% higher than the dissolution rate of the plurality of particles in the aqueous-based solvent without the presence of hydrophobic surface modified nanoparticles. In some other embodiments, the modified dissolution rate in the aqueous-based solvent is lower than the dissolution rate of the plurality of particles in the aqueous-based solvent without the presence of hydrophobic surface modified nanoparticles. In some embodiments, the modified dissolution rate in the aqueous-based solvent is at least 1% lower, at least 5% lower, or even at least 10% lower than the dissolution rate of the plurality of particles in the aqueous-based solvent without the presence of hydrophobic surface modified nanoparticles.

The rate of dissolution of the plurality of particles in an aqueous-based solvent may be monitored by methods known in the art, including monitoring changes in electrical conductivity or UV absorption. Examples of using UV absorption to monitor the rate of dissolution of aspirin, ibuprofen and acetaminophen in aqueous-based solvent are described in USP30-NF25, published Mar. 17, 2008.

Exemplary Embodiments

1. A method of modifying dissolution rate of a plurality of particles, the method comprising:
providing a plurality of particles having a solubility in an aqueous-based solvent;
adding hydrophobic surface modified nanoparticles; and
exposing the plurality of particles to the aqueous-based solvent, wherein the plurality of particles combined with the hydrophobic surface modified nanoparticles have a modified dissolution rate in the aqueous-based solvent relative to a dissolution rate of the plurality of particles in the aqueous-based solvent without the presence of hydrophobic surface modified nanoparticles.
2. The method of embodiment 1, wherein the aqueous-based solvent is water.
3. The method of either embodiment 1 or embodiment 2, wherein the aqueous-based solvent comprises a mixture of water and a water-miscible polar organic solvent.
4. The method of any preceding embodiment, wherein the water-miscible polar organic solvent is selected from the group consisting of a polar organic protic solvent, a polar organic aprotic solvent, and mixtures thereof.
5. The method of embodiment 4, wherein the polar organic protic solvent is an alcohol having up to 6 carbon atoms.
6. The method of embodiment 4, wherein the polar organic aprotic solvent is selected from the group consisting of dimethylsulfoxide, dimethylformamide, N-methylpyrrolidone, acetonitrile, acetone, tetrahydrofuran, and mixtures thereof.
7. The method of any preceding embodiment, wherein the modified dissolution rate in the aqueous-based solvent is higher than the dissolution rate of the plurality of particles in the aqueous-based solvent without the presence of hydrophobic surface modified nanoparticles.
8. The method of any preceding embodiment, wherein the modified dissolution rate in the aqueous-based solvent is at least 10% higher than the dissolution rate of the plurality of particles in the aqueous-based solvent without the presence of hydrophobic surface modified nanoparticles, when tested according to the Method For Measuring Electrical Conductivity Of Samples.
9. The method of any preceding embodiment, wherein the modified dissolution rate in the aqueous-based solvent is lower than the dissolution rate of the plurality of particles in a comparable sample without the presence of hydrophobic surface modified nanoparticles.
10. The method of any preceding embodiment, wherein the modified dissolution rate in the aqueous-based solvent is at least 10% lower than the dissolution rate of the plurality of particles in a comparable sample without the presence of hydrophobic surface modified nanoparticles, when tested according to the Method For Measuring Electrical Conductivity Of Samples.
11. The method of any preceding embodiment, wherein the hydrophobic surface modified nanoparticles are added as discrete hydrophobic surface modified nanoparticles.
12. The method of any preceding embodiment, wherein the hydrophobic surface modified nanoparticles comprise a metal oxide having a hydrophobic surface treatment.
13. The method of embodiment 12, wherein the metal oxide comprises silica.
14. The method of any preceding embodiment, wherein the particles comprise a compound selected from the group consisting of borax, calcium chloride, calcium hydroxide, magnesium chloride, magnesium sulfate, sodium chloride, and sodium sulfite.
15. The method of any preceding embodiment, wherein the particles comprise borax.
16. The method of any one of embodiments 1 to 12, wherein the particles comprise a pharmaceutical agent.
17. The method of any preceding embodiment, wherein the particles further comprise an excipient.
18. The method of any preceding embodiment, wherein the particles have a median particle size of up to 200 micrometers.
19. The method of any preceding embodiment, wherein the particles have a median particle size of up to 75 micrometers.
20. The method of any preceding embodiment, wherein the particles have a median particle size of up to 45 micrometers.
21. The method of any preceding embodiment, wherein the hydrophobic surface modified nanoparticles have a primary particle size of up to 100 nanometers.
22. The method of any preceding embodiment wherein the hydrophobic surface modified nanoparticles have a mean particle size, wherein the particles have a median primary particle size of at least 1 micrometer, and wherein the median primary particle size is in a range from 10 to 10,000 times larger than the mean particle size of the hydrophobic surface modified nanoparticles.
23. The method of any preceding embodiment, wherein the hydrophobic surface modified nanoparticles comprise silica having an organosilane surface treatment.
24. The method of embodiment 23, wherein the organosilane surface treatment comprises isooctyltrimethoxysilane.

EXAMPLES

These examples are for illustrative purposes only and are not meant to be limiting on the scope of the appended claims. All parts, percentages, and ratios in the examples and the rest of the specification are based on weight, unless noted otherwise. Specifically, the term "wt %" means the same as "weight percent" or "percentage by weight". Solvents and other reagents used were obtained from Sigma-Aldrich Chemical Company, St. Louis, Mo., unless otherwise noted.

Materials

The following materials were used in the Examples and Comparative Examples described below.

| Material | Description |
| --- | --- |
| $CaCl_2$ | Anhydrous calcium chloride, obtained from EMD, Gibbstown, NJ |
| $Na_2SO_3$ | Anhydrous sodium sulfite, obtained from Merck, Rahway, NJ |
| Lactose | Alfa Aesar, Ward Hill, MA |
| Borax | Borax pentahydrate, −80/+325 mesh, U.S. Borax, Greenwood Village, CO |
| $MgCl_2.6H2O$ | Magnesium chloride hexahydrate, obtained from EM Cherry Hill, NJ |
| $MgSO_4$ | Anhydrous magnesium sulfate, obtained from Fisher Scientific, Fair Lawn, NJ |
| $Ca(OH)_2$ | Calcium hydroxide, obtained from EMD |
| NaCl | Sodium chloride, obtained from EMD |
| DIW | 18 megohm de-ionized water, obtained by filtration through a filtration system (obtained as an "Ultrapure Water Purification System" from Millipore Corporation, Billerica, MA) |
| DW | Distilled water, obtained from Kandiyohi Co., Chippewa Falls, WI |
| IPA | Isopropyl alcohol |

Method for Preparing Hydrophobic Surface Modified Silica Nanoparticles 100 grams of a silica sol (5 nanometer particle size; 16.6% solids in water; obtained from Nalco Company, Naperville, Ill. under trade designation "NALCO 2326") was added to a 3-neck round-bottom flask (obtained from Ace Glass, Vineland, N.J.). A glass stirring rod with a polytetrafluoroethylene paddle was attached to the center neck of the round-bottom flask. The flask was lowered into an oil bath, and then a condenser was attached, and then the contents stirred. 112.5 grams of an 80:20 wt/wt mixture of ethanol (obtained from EMD Chemicals, Gibbstown, N.J.) and methanol (obtained from VWR International, West Chester, Pa.) was prepared in a 250 milliliter glass beaker. In a 150 milliliter beaker, the following components were added in the following order: half of the 80:20 wt/wt ethanol:methanol mixture, 7.5 grams of isooctyltrimethoxysilane (obtained from Gelest Inc., Morrisville, Pa.) and 0.8 gram of methyltrimethoxysilane (obtained from Sigma-Aldrich Corp., St. Louis, Mo.). The solution was mixed thoroughly and then added to the 3-neck round-bottom flask containing the silica sol ("NALCO 2326"). The remaining half of the 80:20 wt/wt mixture of ethanol and methanol was used to rinse any leftover isooctyltrimethoxysilane or methyltrimethoxysilane from the 150 milliliter beaker into the reaction. The reactants were allowed to stir for 4 hours in the oil bath with the temperature set at 80° C. The resulting surface modified nanoparticles were transferred to a crystallizing dish and dried in an oven set at 150° C. for approximately 1.5 hours. The resulting dried, white product was manually ground up, and then was transferred to a glass jar.

Preparative of Hydrophobic Surface Modified Silica Nanoparticles

For each of Preparative Examples 1-11, a predetermined amount of the indicated particle material to be dissolved was first combined with hydrophobic surface modified silica nanoparticles (prepared as described above) to give the indicated target weight % level, followed by mixing with a laboratory mixer system (obtained under the trade designation "FLACKTEK SPEEDMIXER DAC 150FVZ" from Flack-Tek Inc., Landrum, S.C.) for 1 minute at 3000 rpm, then mixing by hand with a wooden stick, and then remixing for 1 minute at 3000 rpm on the laboratory mixer system. The resulting mixture was then dried in an 80° C. oven for 6 days. Table 1 (below) summarizes the types and amounts of particle materials treated with hydrophobic surface modified silica nanoparticles and the weight % of the hydrophobic surface modified silica nanoparticles for each of Examples 1-11.

TABLE 1

| Preparative Example | Particle material | Particle material amount, grams | Target weight % of hydrophobic SMNP* |
|---|---|---|---|
| 1 | $CaCl_2$ | 3 | 0.1 |
| 2 | $MgSO_4$ | 3 | 0.1 |

TABLE 1-continued

| Preparative Example | Particle material | Particle material amount, grams | Target weight % of hydrophobic SMNP* |
|---|---|---|---|
| 3 | NaCl | 4 | 0.1 |
| 4 | Borax | 3 | 0.04 |
| 5 | Borax | 4 | 0.1 |
| 6 | Borax | 3 | 0.5 |
| 7 | $Ca(OH)_2$ | 8 | 0.05 |
| 8 | $MgCl_2.6H2O$ | 5.5 | 0.01 |
| 9 | $Na_2SO_3$ | 6 | 0.01 |
| 10 | $Na_2SO_3$ | 2.5 | 0.05 |
| 11 | Lactose | 5 | 0.01 |
| 12 | Borax | 3 | 0.04 |
| 13 | Borax | 4 | 0.1 |

*SMNP = surface modified nanoparticles

For each of the particle materials in Comparative Examples A-J (described below), a particle material sample was prepared in the same manner as for the corresponding material in the Preparative Examples above, except that no hydrophobic surface modified silica nanoparticles (SMP) were added.

Method for Measuring Electrical Conductivity of Samples

For each of the Examples and Comparative Examples described below, 125 grams of the indicated aqueous-based solvent was placed in a beaker on a stir plate while stirring continuously with a magnetic stir bar. The initial temperature was recorded, and the initial conductivity of the aqueous-based solvent was measured, prior to addition of particulate material, using a conductivity meter (obtained under the trade designation "MODEL 122 ORION CONDUCTIVITY METER" from Thermo Scientific, Waltham, Mass.) having an conductivity probe (obtained under the trade designation "ORION CONDUCTIVITY PROBE NUMBER 012210" from Thermo Scientific, Waltham, Mass.). Then, a pre-weighed amount (1 gram, unless indicated otherwise) of the indicated material to be tested was added to the aqueous-based solvent while stirring continuously, and the conductivity was measured at roughly 5 second intervals until the conductivity reading stabilized. When the conductivity did not change for a period of 15-30 seconds, it was deemed stabilized. At the end of the conductivity measurements the final temperature was recorded. The initial conductivity, initial temperature, and final temperature for each Example are summarized in Table 2, below.

TABLE 2

| Example | Particle material | wt % of SMNP* | Aqueous-based solvent | Initial Conductivity, microS/cm | Initial Temp., ° C. | Final Temp., ° C. |
|---|---|---|---|---|---|---|
| 1 | $CaCl_2$ | 0.1 | DIW | 5.3 | 23.1 | 24.3 |
| Comp. A | $CaCl_2$ | — | DIW | 4.6 | 23.7 | 24.6 |
| 2 | $MgSO_4$ | 0.1 | DIW | 2.1 | 23.8 | 24.4 |
| Comp. B | $MgSO_4$ | — | DIW | 3.1 | 22.7 | 23.5 |
| 3 | NaCl | 0.1 | DW | 5.7 | 22.4 | 22.3 |
| Comp. C | NaCl | — | DW | 4.2 | 22.5 | 22.4 |
| 4 | Borax | 0.04 | DIW | 1.7 | 23.7 | 24.6 |
| 5 | Borax | 0.1 | DIW | 0.9 | 22.7 | 23.5 |
| 6 | Borax | 0.5 | DIW | 1.9 | 23.8 | 24.4 |
| Comp. D | Borax | — | DIW | 1 | 22.6 | 23.5 |
| 7 | $Ca(OH)_2$ | 0.05 | DIW | 6.3 | 22.5 | 22.8 |
| Comp. E | $Ca(OH)_2$ | — | DIW | 7.4 | 23.0 | 23.0 |
| 8 | $MgCl_2.6H2O$ | 0.01 | DW | 3.4 | 23.0 | 23.1 |
| Comp. F | $MgCl_2.6H2O$ | — | DW | 1.6 | 23.1 | 23.2 |
| 9 | $Na_2SO_3$ | 0.01 | DIW | 2.4 | 23.0 | 23.2 |
| 10 | $Na_2SO_3$ | 0.05 | DIW | 2.0 | 22.9 | 23.0 |
| Comp. G | $Na_2SO_3$ | — | DIW | 1.8 | 23.3 | 23.3 |
| 11 | Lactose | 0.01 | DW | 1.6 | 23.0 | 23.0 |
| Comp. H | Lactose | — | DW | 2.5 | 23.5 | 23.3 |
| 12 | Borax | 0.04 | IPA/DIW (25:75) | 0.7 | 27.4 | 26.1 |
| 13 | Borax | 0.1 | IPA/DIW (25:75) | 0.7 | 28.3 | 27.0 |

TABLE 2-continued

| Example | Particle material | wt % of SMNP* | Aqueous-based solvent | Initial Conductivity, microS/cm | Initial Temp., °C. | Final Temp., °C. |
|---|---|---|---|---|---|---|
| Comp. J | Borax | — | IPA/DIW (25:75) | 0.6 | 28.5 | 27.5 |

*SMNP = surface modified nanoparticles

Example 1 and Comparative Example A

For Example 1, a 1 gram portion of the mixture of anhydrous calcium chloride particle material and 0.1 wt % of surface modified hydrophobic silica nanoparticles (prepared as Preparative Example 1) was added to 125 grams of deionized water, and then the conductivity of this test mixture was measured over time using the "Method For Measuring Electrical Conductivity Of Samples" as described above. The initial conductivity, initial temperature ("Initial Temp."), and the final temperature ("Final Temp.") for Example 1 are indicated in Table 2, above.

For Comparative Example A, the process used for Example 1 was repeated, except that the anhydrous calcium chloride particle material were subjected to the mixing process using the above described laboratory mixer system, but in the absence of hydrophobic silica nanoparticles. The initial conductivity, initial temperature, and final temperature solution for Comparative Example A are indicated in Table 2, above.

Plots of conductivity versus time for Example 1 and Comparative Example A are shown in FIG. 1.

Example 2 and Comparative Example B

Example 2 and Comparative Example B were each run in the same manner as Example 1 and Comparative Example A, respectively, but using anhydrous magnesium sulfate as the particle material. For Example 2, anhydrous magnesium sulfate was treated with hydrophobic surface modified silica nanoparticles at a level of 0.1 wt % (see Preparative Example 2). The initial conductivities, initial temperatures, and final temperatures for Example 2 and Comparative Example B are indicated in Table 2, above.

Figure 2:
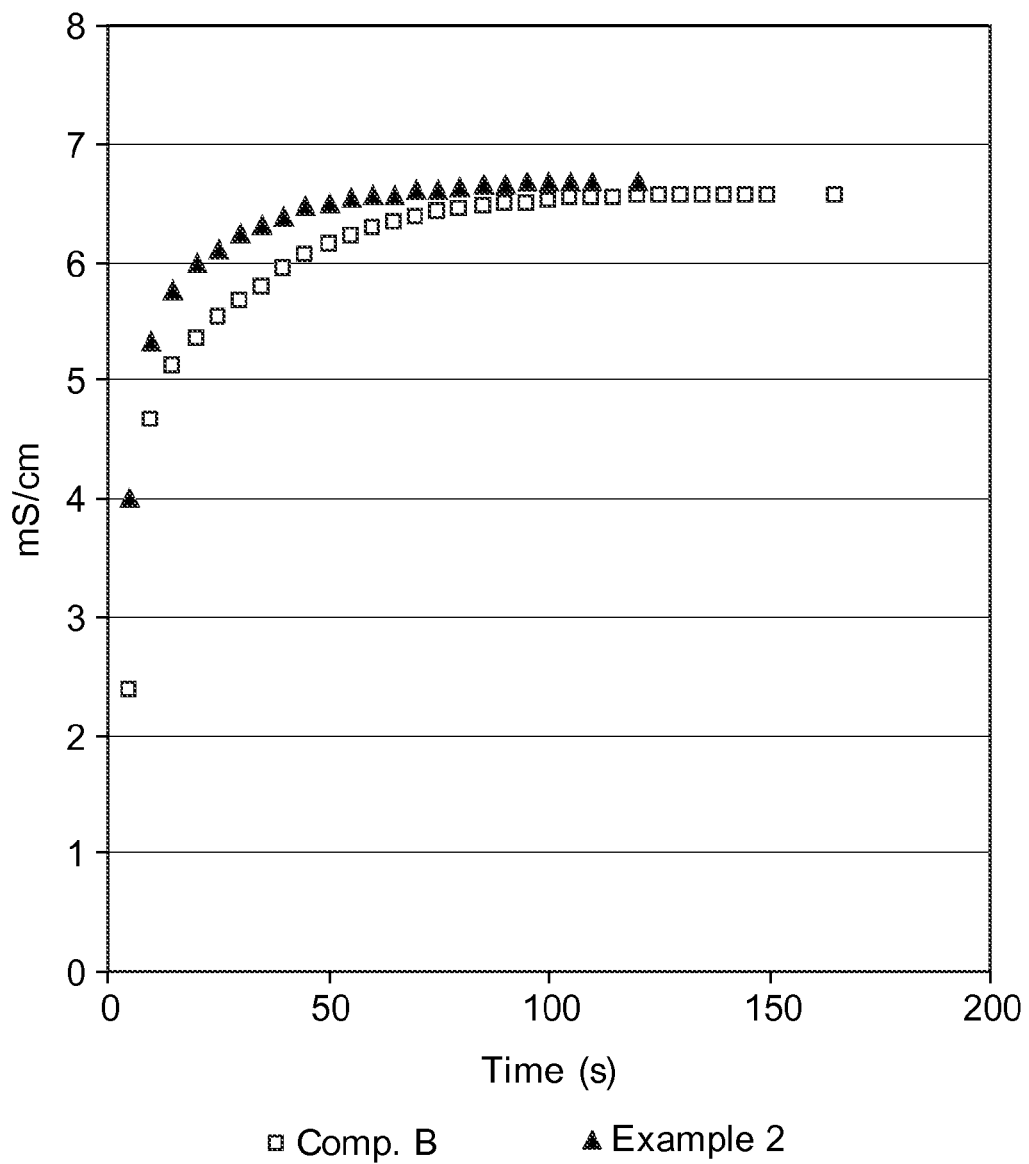
FIG. 2 is a plot of conductance versus time data for Example 2 and Comparative Example B.

Plots of conductivity versus time for Example 2 and Comparative Example B are shown in FIG. 2.

Example 3 and Comparative Example C

Example 3 and Comparative Example C were each run in the same manner as Example 1 and Comparative Example A, respectively, but using sodium chloride as the particle material, and distilled water as the aqueous-based solvent. For Example 3, sodium chloride was treated with hydrophobic surface modified silica nanoparticles at a level of 0.1 wt % (see Preparative Example 3). The initial conductivities, initial temperatures, and final temperatures for Example 3 and Comparative Example C are indicated in Table 2, above.

Figure 3:
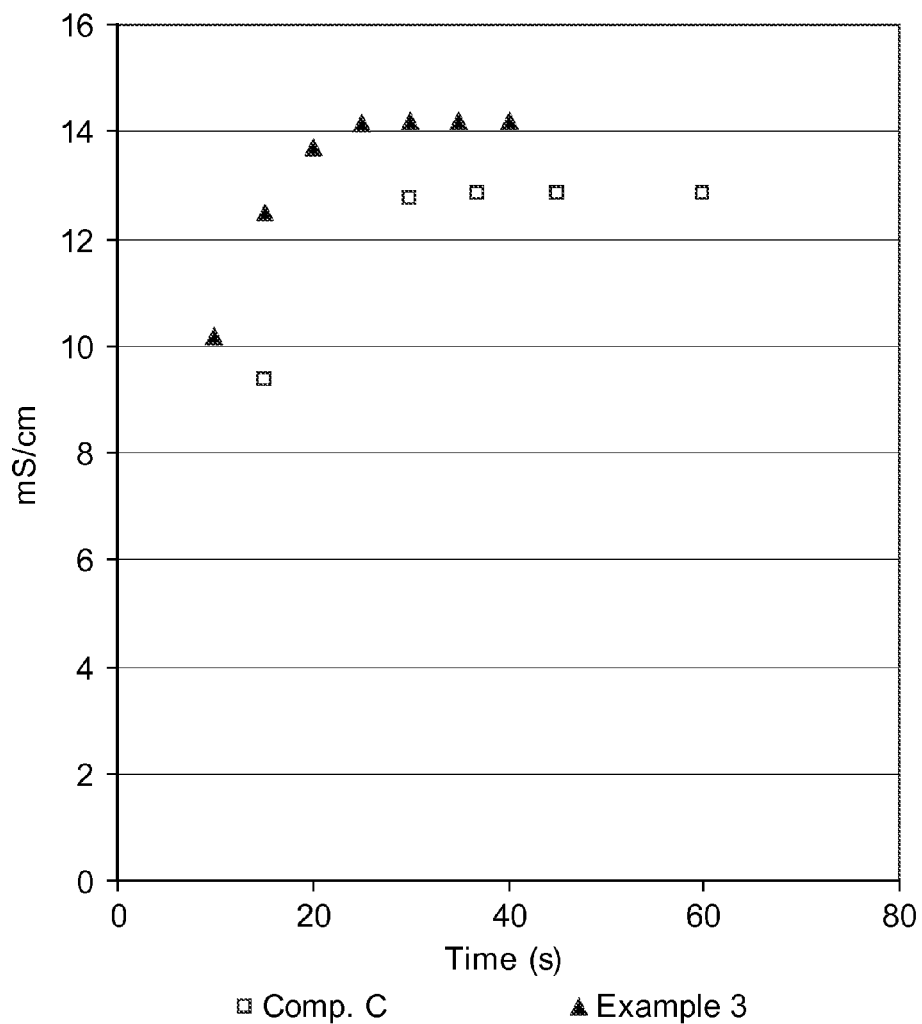
FIG. 3 is a plot of conductance versus time data for Example 3 and Comparative Example C.

Plots of conductivity versus time for Example 3 and Comparative Example C are shown in FIG. 3.

Examples 4, 5, and 6, and Comparative Example D

Examples 4-6 and Comparative Example D were each run in the same manner as Example 1 and Comparative example A, respectively, but using borax as the particle material. For Examples 4, 5, and 6, borax was treated with hydrophobic surface modified silica nanoparticles at levels of 0.04 wt %, 0.1 wt %, and 0.5 wt %, respectively (see Preparative Examples 4, 5, and 6, respectively). The initial conductivities, initial temperatures, and final temperatures for Example 4-6 and Comparative Example D are indicated in Table 2, above.

Figure 4A:
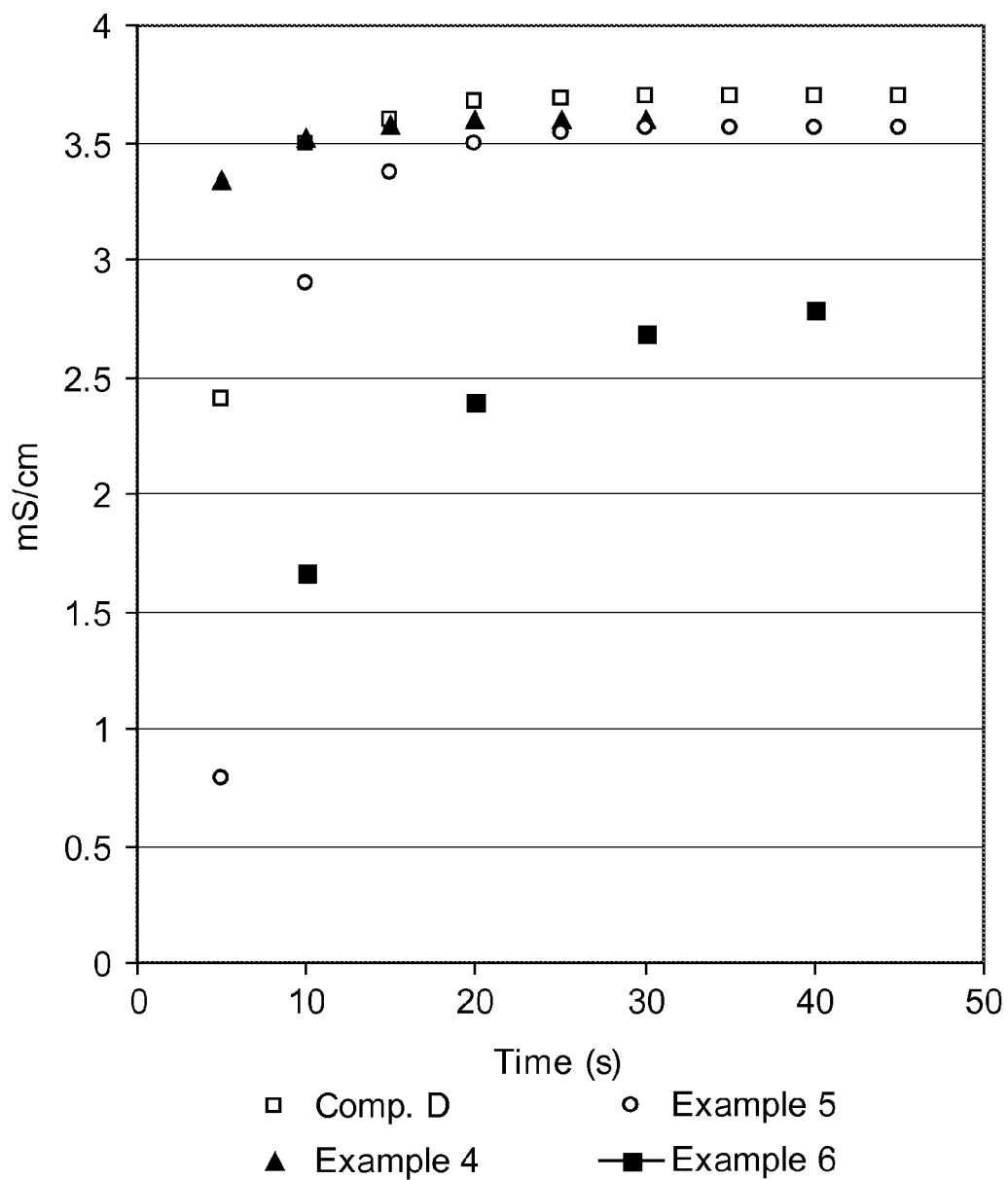
FIGS. 4A and 4B are plots of conductance versus time data for Examples 4-6 and Comparative Example D.
Figure 4B:
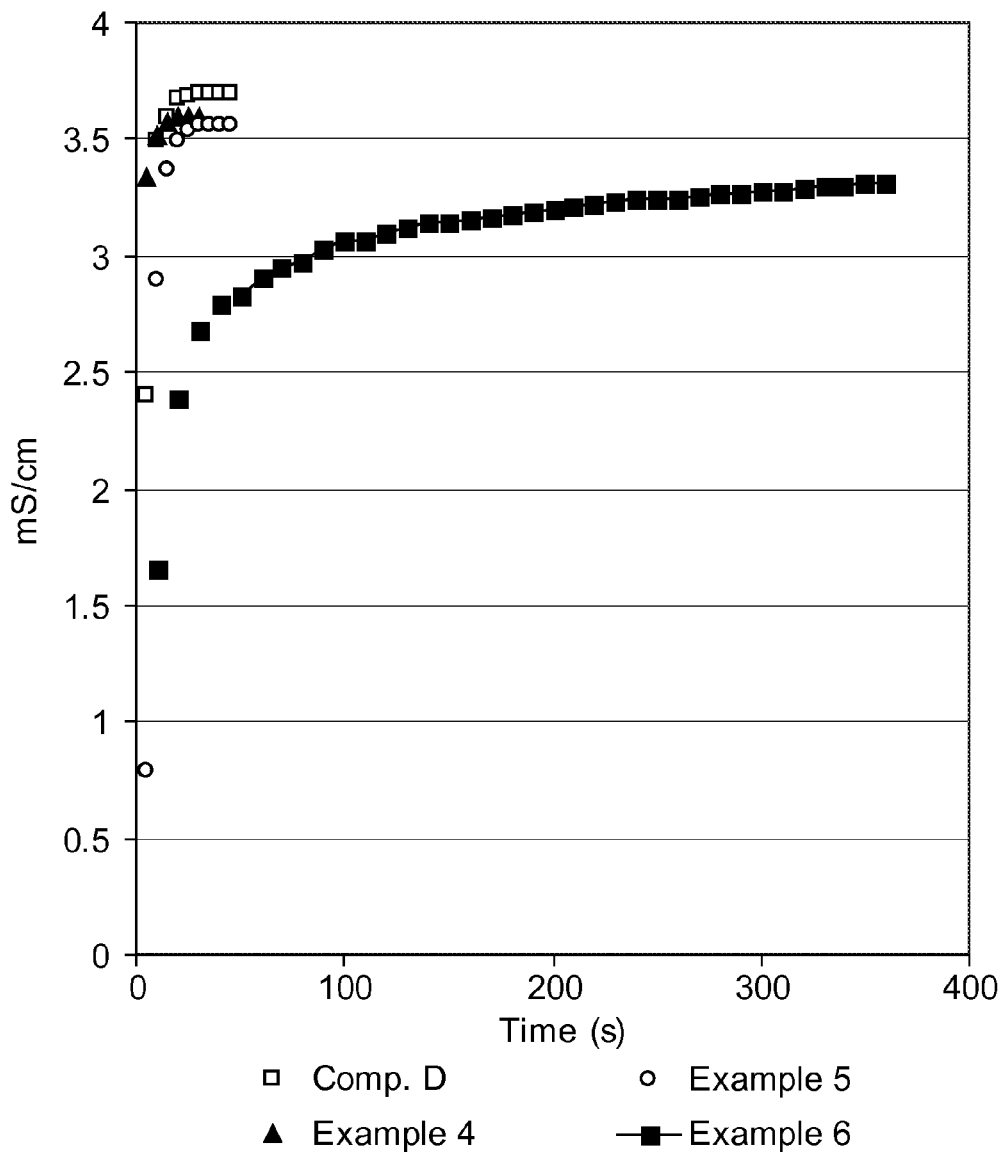

Plots of conductivity versus time for Examples 4-6 and Comparative Example D are shown in FIGS. 4A and 4B. FIG. 4B includes later time points for Example 6 that are not included in FIG. 4A.

Example 7 and Comparative Example E

Example 7 and Comparative Example E were run in the same manner as Example 1 and Comparative Example A, respectively, but using calcium hydroxide as the particle material. For Example 7, calcium hydroxide was treated with hydrophobic surface modified silica nanoparticles at a level of 0.05 wt % (see Preparative Example 7). The initial conductivities, initial temperatures, and final temperatures for Example 7 and Comparative Example E are indicated in Table 2, above.

Figure 5:
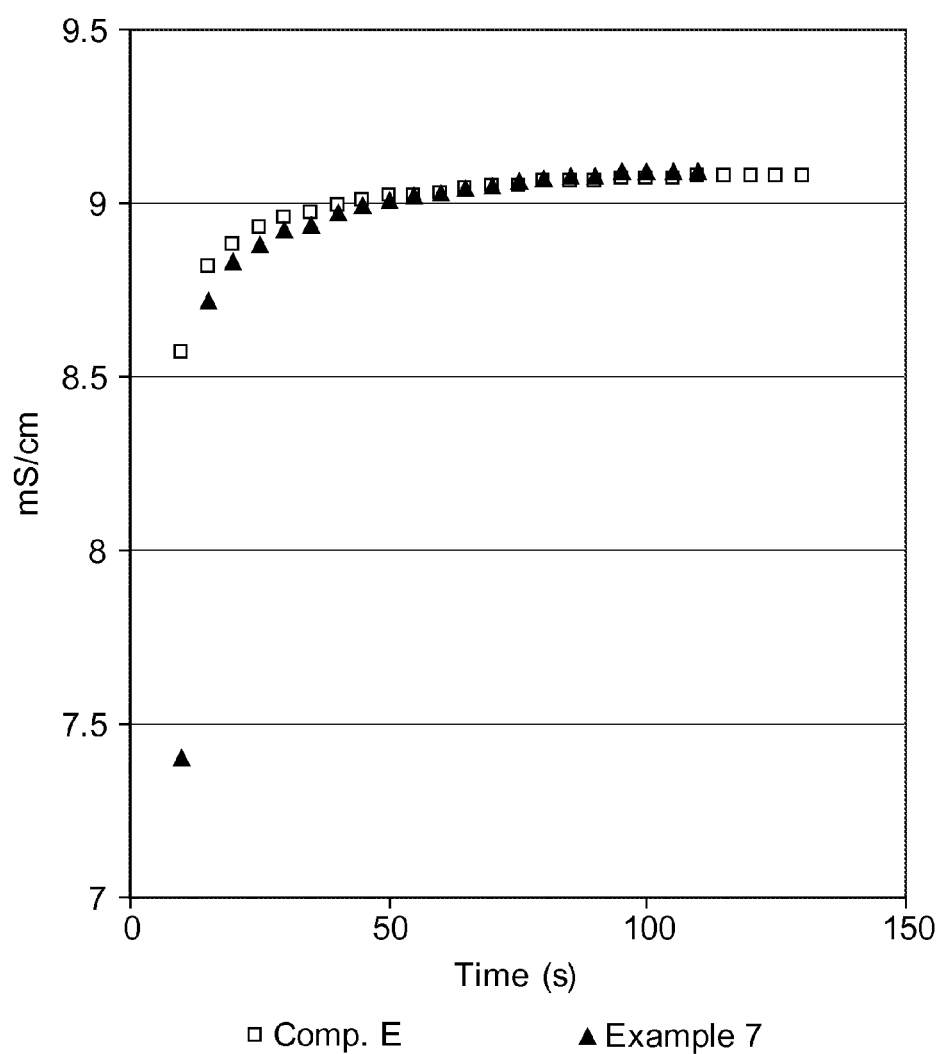
FIG. 5 is a plot of conductance versus time data for Example 7 and Comparative Example E.

Plots of conductivity versus time for Example 7 and Comparative Example E are shown in FIG. 5.

Example 8 and Comparative Example F

Example 8 and Comparative Example F were run in the same manner as Example 1 and Comparative Example A, respectively, but using magnesium chloride hexahydrate as the particle material, and distilled water as the aqueous-based solvent. For Example 8, magnesium chloride hexahydrate was treated with hydrophobic surface modified silica nanoparticles at a level of 0.01 wt % (see Preparative Example 8). The initial conductivities, initial temperatures, and final temperatures for Example 8 and Comparative Example F are indicated in Table 2, above.

Figure 6:
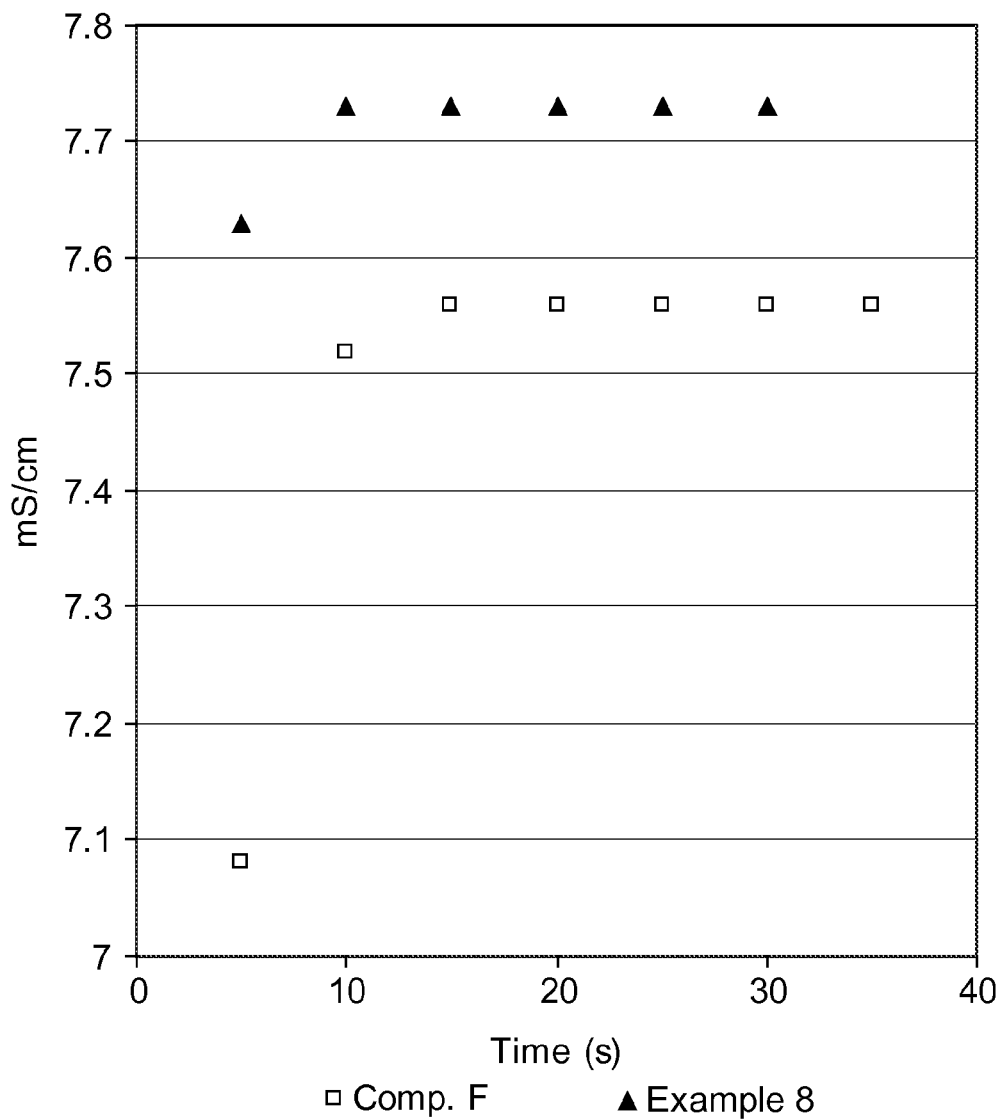
FIG. 6 is a plot of conductance versus time data for Example 8 and Comparative Example F.

Plots of conductivity versus time for Example 8 and Comparative Example F are shown in FIG. 6.

Examples 9-10 and Comparative Example G

Examples 9-10 and Comparative Example E were run in the same manner as Example 1 and Comparative Example A, respectively, but using anhydrous sodium sulfite as the particle material. For Examples 9 and 10, anhydrous sodium sulfite was treated with hydrophobic surface modified silica nanoparticles at levels of 0.01 wt % and 0.05 wt %, respectively (see Preparative Examples 9 and 10, respectively). The initial conductivities, initial temperatures, and final temperatures for Example 9, Example 10 and Comparative Example G are indicated in Table 2, above.

Figure 7:
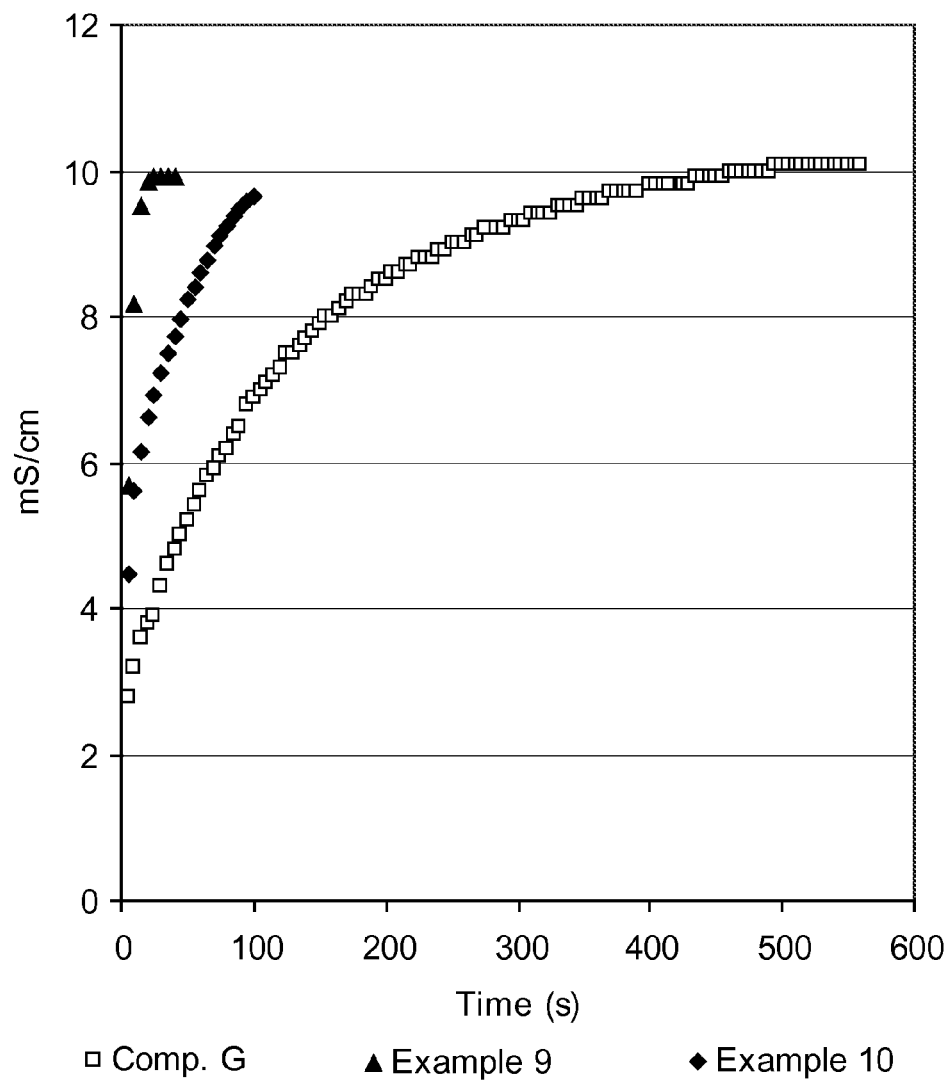
FIG. 7 is a plot of conductance versus time data for Examples 9-10 and Comparative Example G.

Plots of conductivity versus time for Example 9, Example 10, and Comparative Example E are shown in FIG. 7.

Example 11 and Comparative Example H

Example 11 and Comparative Example H were run in the same manner as Example 1 and Comparative Example A, respectively, but using lactose as the particle material. For Example 11, lactose was treated with hydrophobic surface modified silica nanoparticles at a level of 0.01 wt % (see Preparative Example 11). The initial conductivities, initial temperatures, and final temperatures for Example 11 and Comparative Example H are indicated in Table 2, above.

Figure 8:
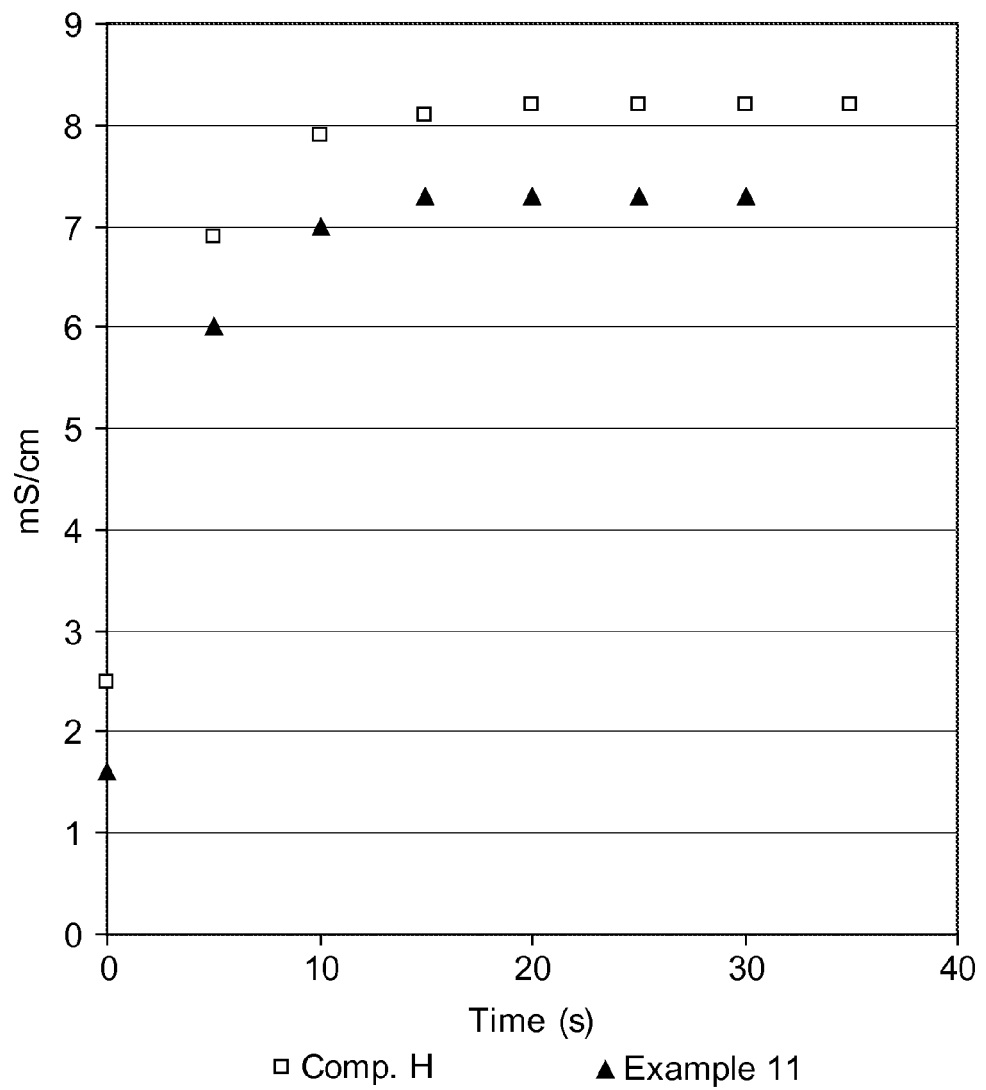
FIG. 8 is a plot of conductance versus time data for Example 11 and Comparative Example H.

Plots of conductivity versus time for Example 11 and Comparative Example H are shown in FIG. 8.

Examples 12-13 and Comparative Example J

Examples 12, 13, and Comparative Example J were run in the same manner as Examples 4, 5, and Comparative Example D, respectively, using borax as the particle material, except that the aqueous-based solvent was a mixture of 25 wt % isopropyl alcohol (IPA) and 75 wt % de-ionized water. For Examples 12 and 13, borax was treated with hydrophobic surface modified silica nanoparticles at levels of 0.04 wt % and 0.1 wt %, respectively (see Preparative Examples 12 and 13, respectively). The initial conductivities, initial temperatures, and final temperatures for Example 12, Example 13, and Comparative Example J are indicated in Table 2, above.

Figure 9:
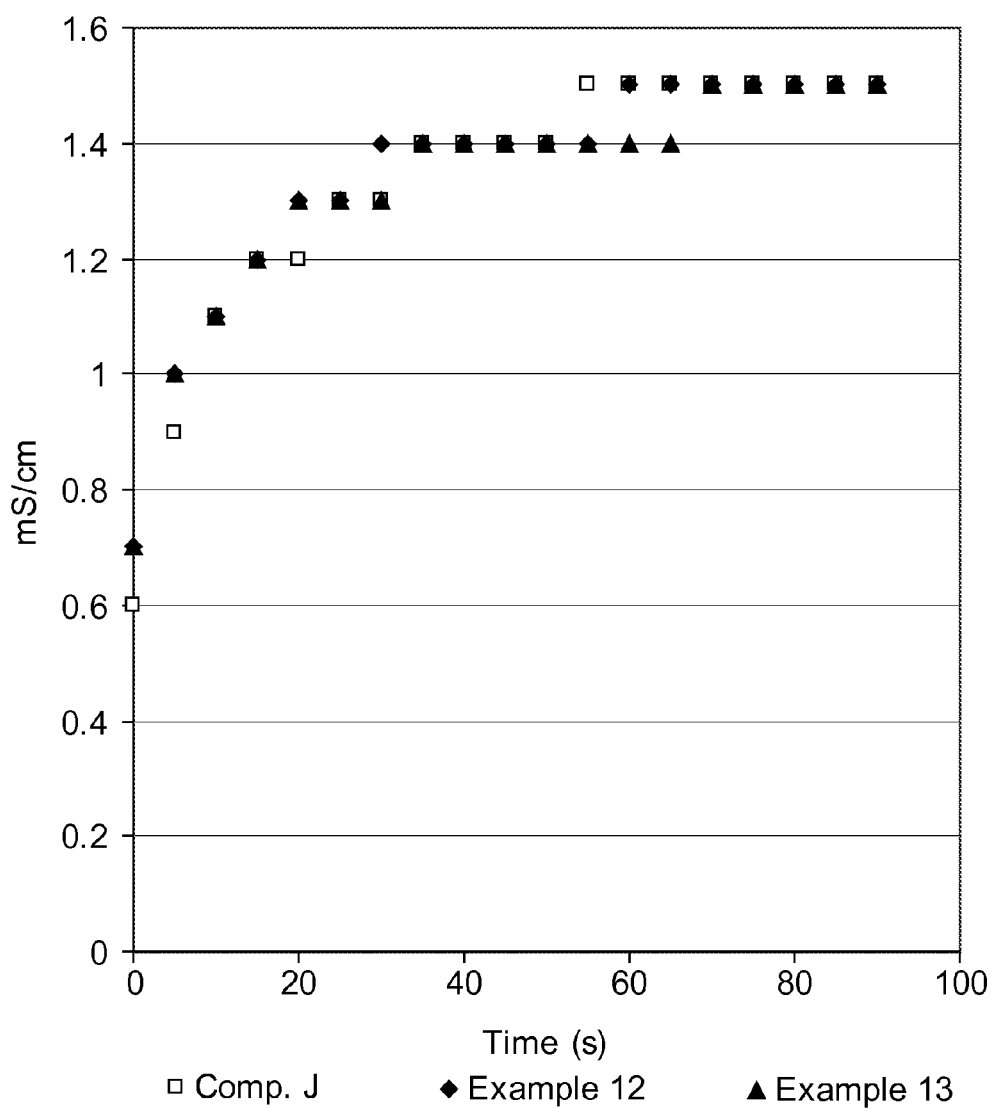
FIG. 9 is a plot of conductance versus time data for Examples 12-13 and Comparative Example J.

Plots of conductivity versus time for Example 12, Example 13, and Comparative Example J are shown in FIG. 9.

Examples Using Acetaminophen

The following procedure (similar to USP30-NF 25, Mar. 17, 2008) was used to measure the rate and intensity of dissolution of acetaminophen and acetaminophen/nanoparticle mixtures in Millipore $H_2O$ (i.e., DIW).

Three samples of acetaminophen were weighed out. One sample was used as a control sample (Comparative K). A pre-determined amount of surface modified nanoparticles were added to each of the other samples. Sample 14 was combined with 1 weight percent nanoparticles (0.013 g) and sample 15 was combined with 0.5 weight percent nanoparticles (0.0065 g). Each blended sample was prepared by adding the nanoparticles to the acetaminophen. Each blended sample was spun in a speed mixer (obtained from FlakTeck, Landrum, S.C., under the trade designation "SPEED-MIXER") at 2×3000 rpm for 1 minute.

TABLE 3

| Sample | Acetaminophen (g) | Nanoparticles (g) |
|---|---|---|
| Comparative K | 1.3 | 0 |
| 14 | 1.3 | 0.013 |
| 15 | 1.3 | 0.0065 |

Each blended sample was then measured separately by adding to different glass beakers, each of which contained 1000 mL of DIW and a magnetic stir-bar. Each glass beaker was placed on a stir plate and stirred at the same setting. 0.013 g of the blended samples were measured out and added to the stirred DIW.

While the acetaminophen was being dissolved in the DIW, 1.5 mL samples of the DIW and acetaminophen mixtures were removed every two minutes by pipette. The UV/Vis spectra of the samples were immediately measured using a UV/Vis spectrophotometer (obtained from PerkinElmer, Waltham, Mass., under the trade designation "LAMBDA 35 UV/VIS SPECTROPHOTOMETER), specifically focusing on the 243 nm absorbance.

Control Sample K exhibited an absorbance intensity of approximately 0.86 at 243 nm. This was determined to be the final measured value needed for subsequent experiments. Once a value of 0.86 was obtained and the absorbance remained constant for at least two intervals, the sampling was stopped.

Figure 10:
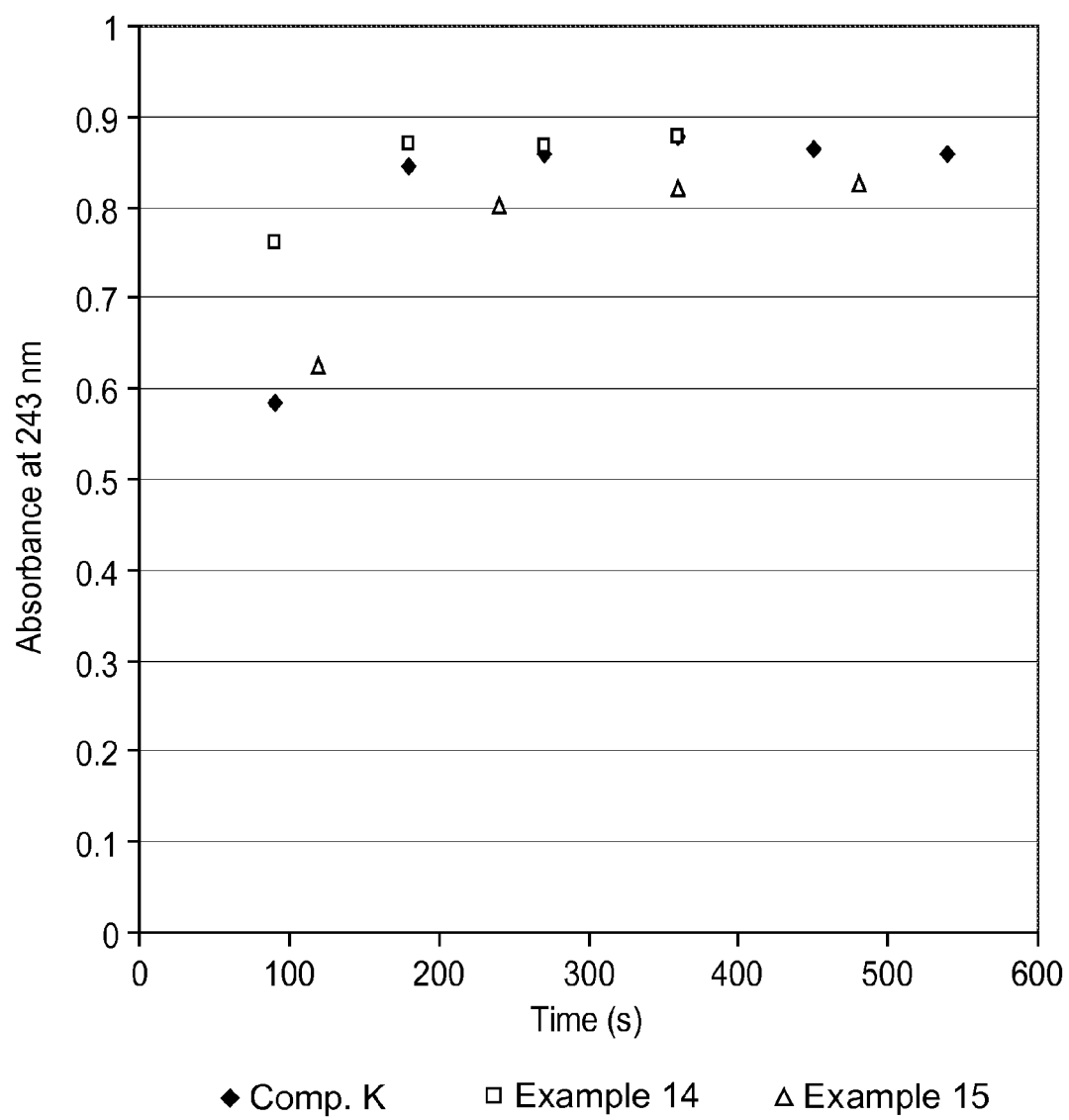
FIG. 10 is a plot of conductance versus time data for Examples 14-15 and Comparative Example K.

The data was then plotted as absorbance vs. time, as in FIG. 10. The slope of the line between the first two time points (change in absorbance at 243 nm/change in time, in seconds) was used for comparing the rates of dissolution among the samples. Those slopes are tabulated in Table 4.

TABLE 4

| Sample | Slope |
|---|---|
| Comparative K | 0.0029 |
| 14 | 0.0015 |
| 15 | 0.0012 |

A smaller slope value implied that the acetaminophen was dissolving faster.

Various modifications and alterations of this invention will become apparent to those skilled in the art without departing from the scope and spirit of this invention.

What is claimed is:

1. A method of increasing the dissolution rate of a plurality of particles, the method comprising:
providing a plurality of particles, the particles having a solubility in an aqueous-based solvent;
adding hydrophobic surface modified nanoparticles; and
exposing the plurality of particles to the aqueous-based solvent, wherein the plurality of particles combined with the hydrophobic surface modified nanoparticles have a modified dissolution rate in the aqueous-based solvent relative to a dissolution rate of the plurality of particles in the aqueous-based solvent without the presence of hydrophobic surface modified nanoparticles.

2. The method of claim 1, wherein the aqueous-based solvent is water.

3. The method of claim 1, wherein the aqueous-based solvent comprises a mixture of water and a water-miscible polar organic solvent.

4. The method of claim 3, wherein the water-miscible polar organic solvent is selected from the group consisting of a polar organic protic solvent, a polar organic aprotic solvent, and mixtures thereof.

5. The method of claim 4, wherein the polar organic protic solvent is an alcohol having up to 6 carbon atoms.

6. The method of claim 4, wherein the polar organic aprotic solvent is selected from the group consisting of dimethylsulfoxide, dimethylformamide, N-methylpyrrolidone, acetonitrile, acetone, tetrahydrofuran, and mixtures thereof.

7. The method of claim 1, wherein the hydrophobic surface modified nanoparticles comprise a metal oxide having a hydrophobic surface treatment.

8. The method of claim 7, wherein the metal oxide comprises silica.

9. The method of claim 1, wherein the particles comprise a compound selected from the group consisting of borax, calcium chloride, calcium hydroxide, magnesium chloride, magnesium sulfate, sodium chloride, and sodium sulfite.

10. The method of claim 1, wherein the particles comprise borax.

11. The method of claim 1, wherein the particles comprise a pharmaceutical agent.

12. The method of claim 1, wherein the particles have a median particle size of up to 200 micrometers.

13. The method of claim 1, wherein the particles have a median particle size of up to 75 micrometers.

14. The method of claim 1, wherein the particles have a median particle size of up to 45 micrometers.

15. The method of claim 1, wherein the hydrophobic surface modified nanoparticles have a primary nanoparticle size of up to 100 nanometers.

16. The method of claim 1 wherein the hydrophobic surface modified nanoparticles have a mean nanoparticle size, wherein the particles have a median primary particle size of at least 1 micrometer, and wherein the median primary particle size is in a range from 10 to 10,000 times larger than the mean nanoparticle size of the hydrophobic surface modified nanoparticles.

17. The method of claim 1, wherein the hydrophobic surface modified nanoparticles comprise silica having an organosilane surface treatment.

18. The method of claim 17, wherein the organosilane surface treatment comprises isooctyltrimethoxysilane.

19. The method of claim 11, wherein the pharmaceutical agent comprises acetaminophen.

20. The method of claim 1 wherein the hydrophobic nanoparticles will be present in an amount up to 10 weight percent solids of the total mixture of particles and nanoparticles.

* * * * *